US 11,485,695 B2

(12) United States Patent
Gillet et al.

(10) Patent No.: US 11,485,695 B2
(45) Date of Patent: Nov. 1, 2022

(54) ALKOXYLATED SECONDARY ALCOHOL

(71) Applicant: Arkema France, Colombes (FR)

(72) Inventors: Jean-Philippe Gillet, Brignais (FR); Thierry Beillon, Sainte Foy les Lyon (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 16/760,564

(22) PCT Filed: Nov. 8, 2018

(86) PCT No.: PCT/FR2018/052761
§ 371 (c)(1),
(2) Date: Apr. 30, 2020

(87) PCT Pub. No.: WO2019/092366
PCT Pub. Date: May 16, 2019

(65) Prior Publication Data
US 2020/0339496 A1 Oct. 29, 2020

(30) Foreign Application Priority Data
Nov. 10, 2017 (FR) ........................................ 1760586

(51) Int. Cl.
C07C 43/00 (2006.01)
C07C 41/00 (2006.01)
C08G 65/00 (2006.01)
C07C 43/13 (2006.01)
C07C 41/03 (2006.01)
C08G 65/26 (2006.01)

(52) U.S. Cl.
CPC .............. *C07C 43/13* (2013.01); *C07C 41/03* (2013.01); *C08G 65/2609* (2013.01); *C08G 65/2663* (2013.01)

(58) Field of Classification Search
CPC .................................. C07C 43/13; C07C 41/03
See application file for complete search history.

(56) References Cited

U.S. PATENT DOCUMENTS

| 3,346,667 A | 10/1967 | Firth |
| 3,395,170 A | 7/1968 | Walts et al. |
| 3,803,238 A | 4/1974 | Struve et al. |
| 5,611,991 A | 3/1997 | Naraghi |
| 6,429,342 B1 | 8/2002 | Clement et al. |
| 6,830,612 B1 | 12/2004 | Yatake et al. |
| 6,977,236 B2 | 12/2005 | Eleveld et al. |
| 2008/0045415 A1 | 2/2008 | Baur et al. |
| 2009/0137752 A1 | 5/2009 | Knott et al. |
| 2010/0122622 A1 | 5/2010 | Takegawa |

FOREIGN PATENT DOCUMENTS

| DE | 4436066 A1 | 4/1996 |
| FR | 2138763 A1 | 1/1973 |
| GB | 758061 | 9/1958 |
| JP | 497212 B1 | 2/1974 |
| JP | 53119809 A | 10/1978 |
| JP | 60119265 A | 6/1985 |
| JP | 01290604 A | 11/1989 |
| JP | 0920874 A | 1/1997 |
| JP | 2009132920 A | 6/2009 |
| JP | 2011105874 A | 6/2011 |
| JP | 2016044299 A | 4/2016 |
| JP | 2017048315 A | 3/2017 |
| WO | 0104183 A1 | 1/2001 |
| WO | 2009000852 A1 | 12/2008 |
| WO | 2009039018 A1 | 3/2009 |
| WO | 2012005897 A1 | 1/2012 |

(Continued)

OTHER PUBLICATIONS

International Search Report and Written Opinion for International Application No. PCT/EP2018/052761, dated Jan. 25, 2019, 9 pages.
International Search Report and Written Opinion for International Application No. PCT/EP2018/052763, dated Apr. 24, 2019, 10 pages.
International Search Report and Written Opinion for International Application No. PCT/EP2018/052762, dated Feb. 12, 2019, 7 pages.
Domingo, X,. "Alcohol and Alcohol Ether Sulfates," 1996, vol. 56, H.W. Stache, pp. 224-279, Anionic Surfactants.
Dekker, M., "Phosphorus-Containing Anionic Surfactants: Organic Chemistry", vol. 56, Marcel Dekker, 1996, pp. 552-564.

(Continued)

*Primary Examiner* — Sikarl A Witherspoon
(74) *Attorney, Agent, or Firm* — RatnerPrestia

(57) ABSTRACT

The invention relates to a compound of following formula (I):

$$R_1 \underset{O}{\overset{R_2}{\diagdown}} \diagdown_{O}\diagup_n \diagdown_{O} \diagdown A \diagdown H \quad (I)$$

a preparation process, uses thereof and compositions containing the same, wherein $R_1$ and $R_2$, represent, independently of one another, a linear, branched or cyclic, saturated or unsaturated hydrocarbon-based group comprising from 1 to 6 carbon atoms, where the sum of the carbon atoms of the groups $R_1$ and $R_2$ ranges from 2 to 7, and where $R_1$ and $R_2$ may also form, together and with the carbon atom bearing them, a 6-, 7-, or 8-membered ring; n is an integer of between 1 and 100, limits included; A represents a sequence of one or more units chosen from ethylene oxide, propylene oxide, butylene oxide units and mixtures thereof; the group formed by $R_1$, $R_2$ and the carbon atom to which $R_1$ and $R_2$ are attached has a degree of branching equal to 0, 1 or 2.

8 Claims, No Drawings

(56) References Cited

FOREIGN PATENT DOCUMENTS

WO        2012071149 A2     5/2012

OTHER PUBLICATIONS

Bakker, "Sulfonates and sulfates of sec-alkyl ethyl ether: detergents prepared by the addition of substituted alcohols to 1-alkenes", Chimie, Physique Et Applications Pratiques Des Agents De Sur Fact, Sep. 9, 1968, pp. 157-165.

Encyclopedia of Chemical Technoiogy, 4th edition, Kirk Othmer, 1997, vol. 23, pp. 146-175.

Encyclopedia of Chemical Technology, 4th edition, Kirk-Othmer, 1997, vol. 23, pp. 504-505.

Johnson et al., "Topical mosquito repellents VII: Alkyl triethylene glycol monoethers", Journal of Pharmaceutical Sciences, Mar. 31, 1975, 64(4):693-695.

Stockburger et al., "The reactions of alkylene oxides with various butyl and other alcohols" JAOC, vol. 40, No. 10, Oct. 1, 1963, pp. 590-594.

Ullmann's Encyclopedia of Industrial Chemistry, 5th edition, Elvers, 8., Hawkins. S., Schulz, G., 1994, vol. A 19, pp. 562-564.

Ullmann's Encyclopedia of Industrial Chemistry, 5th edition, Elvers, 15 B., Hawkins, S., Schulz, G., 1994, vol. A 25, pp. 778-783.

Wang et al., "Synthesis and properties of two surfactants containing polyoxypropylene black and short branched alkyl chain", Journal of Molecular Liquids, Elsevier, Amsterdam, NL, vol. 220, Apr. 26, 2016 (Apr. 26, 2016), pp. 101-107.

Kataoka et al., (1990): STN International CAPLUS database, (Columbus, Ohio), Accession No. 1990: 493313, one page.

Shirai et al., (2011): STN International CAPLUS database, (Columbus, Ohio), Accession No. 2011: 684667, one page.

Kadonome et al., (2014): STN International CAPLUS database, (Columbus, Ohio), Accession No. 2014: 1980740, one page.

Non Final Office Action for U.S. Appl. No. 16/761,379, dated Jan. 7, 2021, 16 pages.

Non Final Office Action for U.S. Appl. No. 16/761,379, dated Oct. 20, 2021, 14 pages.

Sugimoto et al., STN International Caplus database, Accession No. 1975:52646, 1975, 2 pages.

CAS Registry No. 771417-41-5, dated Oct. 28, 2004, 5 pages.

CAS Registry No. 53640-13-4, dated Nov. 16, 1984, 5 pages.

Korean Notice of Grounds for Rejection for Korean Application No. 10-2020-7013149, dated Sep. 3, 2021, 11 pages.

Non Final Office Action for U.S. Appl. No. 16/761,652, dated Oct. 27, 2021, 41 pages.

Japanese Notice of Rejection for Japanese Application No. 2020-525935, dated Apr. 27, 2021, 2 pages.

Non Final Office Action for U.S. Appl. No. 16/761,652, dated May 18, 2022, 11 pages.

ALKOXYLATED SECONDARY ALCOHOL

CROSS-REFERENCE TO RELATED APPLICATIONS

This is the national phase of International Application No. PCT/FR2018/052761, filed 8 Nov. 2018, which claims priority to French Application No. 1760586, filed 10 Nov. 2017. The disclosure of each of these applications is incorporated herein by reference in its entirety for all purposes.

The present invention relates to the general field of alkoxylated secondary alcohols.

Secondary alcohol alkoxylates are a family of compounds which offer a wide range of properties. Indeed, the applications are manifold. They may notably be used as solvent, hydrotrope or nonionic surfactant. They may also act as starting material to other compounds, such as etheramines or anionic surfactants obtained by phosphatation or sulfatation. Thus, secondary alcohol alkoxylates constitute a class of compounds that are of major industrial interest for many players.

Secondary alcohol alkoxylates are conventionally synthesized by means of basic catalysis, for example using potassium hydroxide. Another type of catalyst may also be used: the catalyst of dimetallic cyanide type, known as a DMC catalyst.

Various documents mention the alkoxylation of various compounds, including alcohols, by basic catalysis and/or by DMC catalysis.

For example, WO 2012/071149 describes the ethoxylation of poly-branched secondary alcohols by basic catalysis and/or DMC catalysis. In said document, the secondary alcohols comprise a large number of carbon atoms and numerous branches on the main chain.

Moreover, WO 2009/000852 describes a process for the alkoxylation of various compounds via DMC catalysis. Propylene oxide and/or butylene oxide react first with said compounds, in the presence of a DMC catalyst, and ethylene oxide is then grafted to the synthesized alkoxylate using the DMC catalyst initially present.

WO 2012/005897 notably discloses alcohols that are alkoxylated by means of a propoxyl block, followed by an ethoxyl block, in the presence of a DMC catalyst.

It is moreover known that alcohols of low molecular mass are poisons for the DMC catalyst.

This is one of the reasons for which industrial players favor the alkoxylation of long-chain or very highly branched alcohols to avoid the formation of stable chelates, in the presence of the DMC catalyst.

It should also be noted that industrial players favor a first step of alkoxylation with a propylene oxide and/or butylene oxide block, followed by a second step of alkoxylation using ethylene oxide.

The alkoxylation processes described in the two documents WO 2009/000852 and WO 2012/005897 as mentioned above are moreover performed according to this method.

It is also acknowledged that secondary alcohols have low reactivity when compared with primary alcohols. As a result, the industrialization of products obtained by alkoxylating secondary alcohols has never been reasonably envisaged.

In addition, at a time when the environmental challenges are truly high, it is interesting to envisage using a biobased or biodegradable reagent having a good ecotoxicological profile.

Thus, an alkoxylated, short-chain secondary alcohol is sought, the alkoxylation of which is performed via a simple process that allows low-cost industrial and commercial development. It would also be advantageous to develop alkoxylated secondary alcohols, the starting compound of which is a biobased and biodegradable reagent.

One object of the present invention is to propose a solution for resolving the problems mentioned above.

The subject of the present invention is a compound of formula (I) below:

$$\underset{R_1}{\overset{R_2}{\diagdown}}\!\!\!\!\!\!\!\!\overset{}{\diagup}\;\;\;O\!\!-\!\!\left[\!\!\!\begin{array}{c}\\ \diagdown\!\!\!\diagup\end{array}\!\!\!O\right]_n\!\!\!\!\!-A-H, \qquad (I)$$

in which:

the groups $R_1$ and $R_2$, which may be identical or different, represent, independently of each other, a linear, branched or cyclic, saturated or unsaturated hydrocarbon-based group, comprising from 1 to 6 carbon atoms, it being understood that the sum of the carbon atoms of the groups $R_1$ and $R_2$ ranges from 2 to 7, the groups $R_1$ and $R_2$ may also form, together with the carbon atom that bears them, a 6-, 7- or 8-membered ring, n is an integer between, limits inclusive, 1 and 100, preferably between 2 and 100, more preferably between 3 and 100, particularly between 4 and 100, more particularly between 5 and 100, preferably between 6 and 100, more preferably between 7 and 100, preferably between 8 and 100, more preferably between 9 and 100 and very preferably between 10 and 100.

A represents a sequence of one or more units chosen from ethylene oxide, propylene oxide and butylene oxide units, and mixtures thereof, the group formed by $R_1$, $R_2$ and the carbon atom to which $R_1$ and $R_2$ are attached has a degree of branching equal to 0, 1 or 2.

A subject of the present invention is also a process for preparing the compound of formula (I) according to the invention.

Another subject of the invention is the use of a catalyst of dimetallic cyanide (DMC) type for performing the alkoxylation of 2-octanol.

A subject of the invention is also the use of the compound of formula (I) according to the invention , as nonionic surfactant, low-foaming surfactant, wetting agent, foaming agent, hydrotrope, detergent, solvent, reactive solvent, coalescer, compatibilizer, emulsifying agent, dispersant, chemical intermediary, corrosion inhibitor, demulcent, plasticizer, sequestrants, mineral deposition inhibitor, ionic liquid, stabilizer, lubricant, bitumen additive, deinking additive, oil gellant, ore flotation collector, processing aid in the manufacture of plastics, antistatic agent, fertilizer coating additive, for plant protection, for treating textiles and for enhanced oil recovery, for the production of electrodes and electrolytes for batteries.

Other advantages and characteristics of the invention will become more clearly apparent on examining the detailed description.

It is specified that the expression "from . . . to . . . " used in the present description should be understood as including each of the limits mentioned.

For the purposes of the present invention, the term "ethylene oxide unit" refers to a unit derived from ethylene oxide after opening of the oxirane ring. For the purposes of the present invention, the term "propylene oxide unit" refers to a unit derived from propylene oxide after opening of the oxirane ring. For the purposes of the present invention, the term "butylene oxide unit" refers to a unit derived from butylene oxide after opening of the oxirane ring.

The compound according to the invention is of formula (I) as mentioned above.

In other words, the groups $R_1$ and $R_2$, and the carbon atom to which they are attached, denote a C3-C8, preferably C4-C8, more particularly C5-C8, preferably C6-C8, secondary radical.

Preferably, the groups $R_1$ and $R_2$, which may be identical or different, represent, independently of each other, methyl, ethyl, n-propyl, isopropyl, n-butyl, sec-butyl, pentyl or hexyl.

Preferably, the group formed by $R_1$, $R_2$ and the carbon atom to which $R_1$ and $R_2$ are attached is chosen from the 2-octyl radical and the 4-methyl-2-pentyl radical. More particularly, the group formed by $R_1$, $R_2$ and the carbon atom to which $R_1$ and $R_2$ are attached is the 2-octyl radical.

Advantageously, n is between, limits inclusive, 1 and 75, preferably between 2 and 75, more preferably between 3 and 75, particularly between 4 and 75, more particularly between 5 and 75, preferably between 6 and 75, more preferably between 7 and 75, preferably between 8 and 75, more preferably between 9 and 75 and very preferably between 10 and 75.

Advantageously, n is between, limits inclusive, 1 and 50, preferably between 2 and 50, more preferably between 3 and 50, particularly between 4 and 50, more particularly between 5 and 50, preferably between 6 and 50, more preferably between 7 and 50, preferably between 8 and 50, more preferably between 9 and 50 and very preferably between 10 and 50.

Advantageously, n is between, limits inclusive, 1 and 30, preferably between 2 and 30, more preferably between 3 and 30, particularly between 4 and 30, more particularly between 5 and 30, preferably between 6 and 30, more preferably between 7 and 30, preferably between 8 and 30, more preferably between 9 and 30 and very preferably between 10 and 30. Preferably, n ranges from 2 to 30.

For the purposes of the present invention, the degree of branching denotes the total number of terminal methyl groups ($—CH_3$) present on the groups $R_1$ and $R_2$ minus 1. In other words, the degree of branching, denoted as D, is an integer equal to the difference between the sum of the terminal methyl groups ($—CH_3$) present on the groups $R_1$ and $R_2$ and 1. This equation may be expressed as follows:

$$D = \Sigma(\text{Me in } R_1 \text{ and } R_2) - 1$$

Thus, if the groups $R_1$ and $R_2$ comprise 2 methyl groups, the degree of branching is then 1.

$$D = \Sigma(\text{Me in R1 et R2}) - 1 = 2 - 1 = 1$$

Preferably, the degree of branching is 1 or 2.

For example, the degree of branching of the 2-octyl radical is 1 and the degree of branching of the 4-methyl-2-pentyl radical is 2.

The compound of formula (I) comprises n ethylene oxide units, and a sequence including one or more units chosen from ethylene oxide, propylene oxide and butylene oxide units, and mixtures thereof.

According to a particular embodiment, when the compound of formula (I) includes a mixture of said different units, they may be distributed randomly, alternately or in blocks.

In a preferred embodiment of the invention, the compound of formula (I) comprises n ethylene oxide units and a sequence including one or more units chosen from ethylene oxide, propylene oxide and butylene oxide units, and mixtures thereof, said units possibly being distributed randomly, alternately or in blocks, at least one propylene oxide or butylene oxide unit being present in said sequence.

According to another preferred embodiment, A represents a sequence comprising at least one ethylene oxide unit and of at least one propylene oxide unit, distributed alternately, randomly or in blocks.

According to yet another preferred embodiment, A represents a sequence comprising at least one ethylene oxide unit and of at least one butylene oxide unit, distributed alternately, randomly or in blocks.

According to yet another preferred embodiment, A represents a sequence comprising at least one propylene oxide unit and of at least one butylene oxide unit, distributed alternately, randomly or in blocks.

A subject of the invention is also a process for preparing a compound of formula (I) as defined previously, comprising the following successive steps:
(a) reacting a secondary alcohol of formula (II) below:
    $R_1CH(OH)R_2$ (II), in which $R_1$ and $R_2$ are as defined previously, with n ethylene oxide(s), where n is as defined previously, in the presence of at least one catalyst of dimetallic cyanide type;
(b) reacting the product obtained from step (a) with one or more oxides chosen from ethylene oxide, propylene oxide and butylene oxide, and mixtures thereof, in the presence of at least one catalyst of dimetallic cyanide type.

Optionally, the product obtained from step (a) may be isolated. The process according to the invention has the advantage of synthesizing the compound of formula (I) under good safety conditions, which means that it can be performed on an industrial scale. Specifically, the operating conditions in terms of temperature and pressure are controlled by means of the process according to the invention. The exothermicity of the reaction is notably controlled.

The secondary alcohol of formula (II) has a degree of branching of 0, 1 or 2. Advantageously, the secondary alcohol of formula (II) has a weight-average molar mass ranging from 70 to 200 g/mol, preferably from 80 to 180 g/mol. The secondary alcohol of formula (II) is a C3-C8 and preferably C6-C8 alcohol.

The secondary alcohol of formula (II) may be chosen from 2-octanol and methylisobutylcarbinol, preferably 2-octanol. This alcohol is of particular interest in several respects. Specifically, it is a biobased, biodegradable product and has a good ecotoxicological profile. In addition, the boiling point of 2-octanol is high and its cost price is entirely reasonable.

According to a preferred embodiment, the secondary alcohol of formula (II) is used after drying, such that the water content in said alcohol is less than or equal to 200 ppm, preferably less than or equal to 100 ppm.

Preferably, the catalyst of dimetallic cyanide type may be of any nature known to a person skilled in the art. These catalysts are described in patents U.S. Pat. Nos. 6,429,342, 6,977,236 and PL 398 518. More particularly, the catalyst used is zinc hexacyanocobaltate, which is sold, for example, by the company Bayer under the name Arcol® or by the company Mexeo under the name MEO-DMC®.

Advantageously, the content of catalyst of dimetallic cyanide type ranges from 1 to 1000 ppm relative to the content of secondary alcohol of formula (II), preferably from 1 to 500 ppm, preferably from 2 to 300 ppm, more preferentially from 5 to 200 ppm.

According to a preferred embodiment, the ethylene oxide/secondary alcohol of formula (II) mole ratio ranges from 1 to 100, preferably from 2 to 100, preferably from 3 to 100, preferably from 4 to 100, particularly from 5 to 100, more particularly from 6 to 100, preferably from 7 to 100, even more preferably from 8 to 100, preferentially from 9 to 100 and preferably from 10 to 100.

Preferably, the reaction temperature during step (a) ranges from 80 to 200° C., preferably from 100 to 180° C. The reaction pressure during step (a) may range from 0.01 MPa to 3 MPa, preferably from 0.02 MPa to 2 MPa.

Preferably, the reaction temperature during step (b) ranges from 80 to 200° C., preferably from 100 to 180° C. The reaction pressure during step (b) may range from 0.01 MPa to 3 MPa, preferably from 0.02 MPa to 2 MPa.

The duration of each of the steps (a) and (b) may range from a few minutes to a few hours, typically 5 minutes to 24 hours.

Preferably, the process according to the invention comprises a step of removing the residual oxides chosen from ethylene oxide, propylene oxide and butylene oxide, and mixtures thereof, used during the process according to the invention. Thus, this step may proceed between step (a) and step (b) and also after step (b).

For the purposes of the present invention, the term "residual oxide" means an oxide which has not reacted. Preferably, said step of removing the residual oxide is performed by cooking, i.e. by maintaining a temperature ranging from 70° C. to 170° C., preferentially from 100° C. to 160° C., in order to consume the residual oxide, and/or by means of a stripping step under an inert gas stream. Alternatively, said stripping step may be performed under vacuum.

Preferably, after said removal step, the mass content of residual oxide is less than or equal to 0.1% relative to the weight of compound of formula (I) obtained, preferentially less than or equal to 0.01%, more preferentially less than or equal to 0.001%.

Preferably, the process according to the invention comprises the following successive steps:
(a1) mixing in a reactor at least one secondary alcohol of formula (II), preferably dried beforehand as described previously, and at least one catalyst of dimetallic cyanide type;
(a2) gradually adding to the mixture n ethylene oxide(s), to obtain the ethoxylated secondary alcohol of formula (I);
(a3) maintaining the reaction temperature until the pressure has stabilized;
(a4) adding to the mixture one or more oxides chosen from ethylene oxide, propylene oxide and butylene oxide, and mixtures thereof;
(a5) maintaining the reaction temperature until the pressure has stabilized;
(a6) recovering the expected product after optional (but preferred) stripping.

Preferably, the process according to the invention comprises the following successive steps:
(a1) mixing in a reactor at least one secondary alcohol of formula (II), preferably dried beforehand as described previously, and at least one catalyst of dimetallic cyanide type;
(a2) gradually adding to the mixture n ethylene oxide(s), to obtain the ethoxylated secondary alcohol of formula (I);
(a3) maintaining the reaction temperature until the pressure has stabilized;
(a4) adding to the mixture one or more oxides chosen from propylene oxide and butylene oxide, and mixtures thereof;
(a5) maintaining the reaction temperature until the pressure has stabilized;
(a6) adding to the mixture one or more oxides chosen from ethylene oxide, propylene oxide and butylene oxide, and mixtures thereof;
(a7) maintaining the reaction temperature until the pressure has stabilized;
(a8) recovering the expected product after optional (but preferred) stripping.

Moreover, the process may be performed batchwise, semi-continuously or continuously. A person skilled in the art will know how to adapt the process for manufacturing the compound of formula (I) according to the invention according to the random, alternating or block distribution of the sequence A.

A subject of the invention is also the use of a catalyst of dimetallic cyanide type for performing the alkoxylation of 2-octanol.

A subject of the invention is also the use of the compound of formula (I) as defined previously, as nonionic surfactant, low-foaming surfactant, wetting agent, foaming agent, hydrotrope, detergent, solvent, reactive solvent, coalescer, compatibilizer, emulsifying agent, dispersant, chemical intermediary, corrosion inhibitor, demulcent, plasticizer, sequestrant, mineral deposition inhibitor, ionic liquid, stabilizer, lubricant, bitumen additive, deinking additive, oil gellant, ore flotation collector, processing aid in the manufacture of plastics, antistatic agent, fertilizer coating additive, for plant protection, for treating textiles and for enhanced oil recovery, for the production of electrodes and electrolytes for batteries.

A subject of the present invention is also a composition comprising at least one compound of formula (I) as defined previously, and one or more aqueous, organic or aqueous-organic solvents, for instance water, alcohols, glycols, polyols, mineral oils, plant oils, and the like, alone or as mixtures of two or more thereof, in all proportions.

The composition according to the invention may also contain one or more additives and fillers that are well known to those skilled in the art, for instance, in a nonlimiting manner, anionic, cationic, amphoteric or nonionic surfactants, rheology modifiers, demulcents, deposition-inhibiting agents, antifoams, dispersants, pH control agents, colorants, antioxidants, preserving agents, corrosion inhibitors, biocides, and other additives, for instance sulfur, boron, nitrogen or phosphate products, and the like. The nature and amount of the additives and fillers may vary within wide proportions depending on the nature of the intended application and may readily be adapted by a person skilled in the art.

The invention is illustrated by the following examples, which are not in any way limiting.

EXAMPLES

The 2-octanol (CAS RN 123-96-6) used is the "refined" grade 2-octanol Oleris® (purity >99%), sold by Arkema France.

Example 1: Ethoxylation of 2-octanol 619 g (4.76 M) of 2-octanol dried to less than 200 ppm of water and 0.06 g (100 ppm) of catalyst DMC Arcol® are placed in a clean, dry 4 L autoclave. The reactor is closed and purged with nitrogen and the leaktightness under pressure is checked. The reactor is pressurized with nitrogen to 0.269 MPa at 20° C.

The reaction medium is brought to 120° C. with stirring. At this temperature of 120° C., 40 g of ethylene oxide are introduced. When initiation of the reaction is observed, the rest of the ethylene oxide is introduced, i.e. 628 g (14.27 M) in total over 60 minutes at a temperature of 140° C.-150° C. At the end of the addition, the temperature is maintained for 30 minutes and the residual ethylene oxide is then stripped out with nitrogen. The reactor is cooled to 60° C. and 1240 g of alkoxylated 2-octanol comprising 3 ethylene oxide units are recovered. The hydroxyl number (OHN) is 210 mg of KOH/g and the coloration is 26 Hz.

Example 2: Ethoxylation of methylisobutylcarbinol (MIBC)

441 g (4.32 M) of MI BC dried to less than 200 ppm of water and 0.044 g (100 ppm) of catalyst DMC Arcol® are placed in a clean, dry 4 L autoclave. The reactor is closed and purged with nitrogen and the leaktightness under pressure is checked. The reactor is pressurized with nitrogen to 0.246 MPa at 28° C.

The reaction medium is brought to 120° C. with stirring. At this temperature of 120° C., 40 g of ethylene oxide are introduced. When initiation of the reaction is observed at 141° C., the rest of the ethylene oxide is introduced, i.e. 380 g (8.64 M) in total over 40 minutes at a temperature of 140° C.-150° C. At the end of the addition, the temperature is maintained for 60 minutes and the residual ethylene oxide is then stripped out with nitrogen. The reactor is cooled to 60° C. and 815 g of alkoxylated methylisobutylcarbinol comprising 2 ethylene oxide units are recovered. (OHN): 290 mg of KOH/g and coloration: 3 Hz).

Example 3: Ethoxylation-propoxylation of 2-octanol 1034 g (7.95 M) of 2-octanol dried to less than 200 ppm of water and 0.15 g (145 ppm) of catalyst DMC Arcol® are placed in a clean, dry 10 L autoclave. The reactor is closed and purged with nitrogen and the leaktightness under pressure is checked. The reactor is pressurized with nitrogen to 0.12 MPa at 27° C.

The reaction medium is brought to 120° C. with stirring. At this temperature of 120° C., 35 g of ethylene oxide are introduced. When initiation of the reaction is observed, the rest of the ethylene oxide is introduced, i.e. 2098 g (47.68 M) in total over 4 hours at a temperature of 140° C.-150° C. At the end of the addition, the temperature is maintained for 30 minutes to consume the residual ethylene oxide. A sample of the intermediate product withdrawn for analysis indicates the following features: OHN=136 mg of KOH/g and coloration of 39 Hz.

The reaction is continued by introducing propylene oxide, i.e. 1844 g (31.18 M) in total over 3 hours. At the end of the reaction, the temperature is maintained at 140° C. for 30 minutes to consume the residual propylene oxide, the system is then purged and degassed, and 4910 g of 2-octanol-60E-4P0 are recovered. OHN=86 mg of KOH/g and coloration of 44 Hz.

The invention claimed is:
1. A compound of formula (I) below:

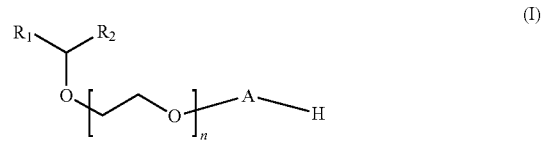

wherein:
$R_1$ and $R_2$ form, together with the carbon atom to which $R_1$ and $R_2$ are attached, a 2-octyl radical;
n is an integer between, limits inclusive, 1 and 100; and
A represents a sequence of one or more units selected from the group consisting of ethylene oxide, propylene oxide, butylene oxide units, and mixtures thereof.

2. A process for preparing a compound of formula (I) as defined in claim 1, comprising the following successive steps:
mixing in a reactor at least one secondary alcohol of formula (II) below:

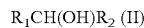

and at least one dimetallic cyanide catalyst, wherein $R_1$ and $R_2$ are as defined in claim 1 and where the secondary alcohol was previously dried to contain to less than 200 ppm of water,
gradually adding to the mixture n ethylene oxide(s), where n is an integer between, limits inclusive, 1 and 100;
maintaining reaction temperature until reaction pressure has stabilized;
removing any residual ethylene oxide from the reactor;
adding one or more oxides selected from the group consisting of ethylene oxide, propylene oxide and butylene oxide, and mixtures thereof;
maintaining reaction temperature until reaction pressure has stabilized; and
recovering the compound of formula (I) after optional removal of any residual ethylene oxide, propylene oxide, butylene oxide and mixtures thereof.

3. The process as claimed in claim 2, wherein the dimetallic cyanide catalyst is zinc hexacyanocobaltate.

4. The process as claimed in claim 2, wherein the content of the dimetallic cyanide catalyst ranges from 1 to 1000 ppm relative to the content of the secondary alcohol of formula (II).

5. The process as claimed in claim 2, wherein the ethylene oxide/secondary alcohol of formula (II) mole ratio ranges from 2 to 100.

6. A method for alkoxylating 2-octanol comprising:
mixing in a reactor 2-octanol and at least one dimetallic cyanide catalyst, where the 2-octanol was previously dried to contain to less than 200 ppm of water,
gradually adding to the mixture n ethylene oxide(s), where n is an integer between, limits inclusive, 1 and 100;
maintaining reaction temperature until reaction pressure has stabilized;
removing any residual ethylene oxide from the reactor;
adding one or more oxides selected from the group consisting of ethylene oxide, propylene oxide and butylene oxide, and mixtures thereof;
maintaining reaction temperature until reaction pressure has stabilized; and recovering the alkoxylate octanol after optional removal of any residual ethylene oxide, propylene oxide, butylene oxide and mixtures thereof.

7. A nonionic surfactant, low-foaming surfactant, wetting agent, foaming agent, hydrotrope, detergent, solvent, reactive solvent, coalescer, compatibilizer, emulsifying agent, dispersant, chemical intermediary, corrosion inhibitor, demulcent, plasticizer, sequestrant, mineral deposition inhibitor, ionic liquid, stabilizer, lubricant, bitumen additive, deinking additive, oil gellant, ore flotation collector, processing aid, antistatic agent or fertilizer coating additive comprising the compound of formula (I) as defined in claim 1.

8. A composition comprising at least one compound of formula (I) as defined in claim 1, and one or more aqueous, organic or aqueous-organic solvents, optionally with one or more additives and fillers.

\* \* \* \* \*